(12) United States Patent
Grossmann et al.

(10) Patent No.: US 8,358,884 B2
(45) Date of Patent: Jan. 22, 2013

(54) MICROOPTICAL COMPONENT AND METHOD FOR ITS MANUFACTURE

(75) Inventors: Tobias Grossmann, Karlsruhe (DE); Mario Hauser, Bruchsal (DE); Torsten Beck, Karlsruhe (DE); Heinz Kalt, Stutensee (DE); Christoph Vannahme, Karlsruhe (DE); Timo Mappes, Karlsruhe (DE)

(73) Assignee: Karlsruher Institut fuer Technologie, Karlsruhe (DE)

( * ) Notice: Subject to any disclaimer, the term of this patent is extended or adjusted under 35 U.S.C. 154(b) by 340 days.

(21) Appl. No.: 12/860,354

(22) Filed: Aug. 20, 2010

(65) Prior Publication Data

US 2011/0044581 A1  Feb. 24, 2011

(30) Foreign Application Priority Data

Aug. 22, 2009  (EP) .................................... 09010782

(51) Int. Cl.
  *G02B 6/26* (2006.01)
(52) U.S. Cl. .......................................... 385/30; 385/130
(58) Field of Classification Search .................. None
  See application file for complete search history.

(56) References Cited

U.S. PATENT DOCUMENTS

| 566,790 | A | 9/1896 | McLean |
| 7,062,118 | B2 | 6/2006 | Chiu et al. |
| 7,106,429 | B2 | 9/2006 | Zhou et al. |
| 7,693,369 | B2 | 4/2010 | Fan et al. |
| 7,781,217 | B2 | 8/2010 | Armani et al. |
| 2005/0013529 | A1 | 1/2005 | Chiu et al. |
| 2005/0162656 | A1 | 7/2005 | Zhou et al. |
| 2007/0237460 | A1 | 10/2007 | Fan et al. |
| 2007/0269901 | A1 | 11/2007 | Armani et al. |

FOREIGN PATENT DOCUMENTS

| WO | WO 0208815 A1 | 1/2002 |
| WO | WO 2005019798 A2 | 3/2005 |
| WO | WO 2006108096 A2 | 10/2006 |

OTHER PUBLICATIONS

Armani et al., Label-Free, Single-Molecule Detection with Optical Microcavities, Science 317, pp. 783-786, 2007, obtained from internet on Aug. 27, 2010 at http://www.vahala.caltech.edu/html/recent_publications.html.
Armani et al., Ultra-high-Q toroid microcavity on a chip, Nature 421, pp. 925-928, 2003.
Lai et al., Silica on Si waveguides for self-aligned fibre array coupling using flip-chip Si V-groove technique, Electronics Letters 32, pp. 1916-1917, 1996.
Laine et al., Design and Applications of Optical Microsphere Resonators, Dissertation, Helsinki University of Technology, pp. 20-21, 2003, obtained from internet on Aug. 27, 2010 at http://lib.tkk.fi/Diss/2003/isbn951226448X/isbn951226448X.pdf.
Liu et al., Long-period gratings in polymer ridge waveguides, Optics Express 13, pp. 1150-1160, 2005.

*Primary Examiner* — Jerry Rahll
(74) *Attorney, Agent, or Firm* — Leydig, Voit & Mayer, Ltd.

(57) ABSTRACT

A microoptical component for coupling a laser light to microresonators includes at least two microresonators, each having a form of an axially symmetric body disposed on a pedestal, and at least one waveguide for the laser light. The at least two microresonators are disposed on a first substrate having first side walls. The at least one waveguide is disposed on a second substrate having second side walls. The first side walls and the second side walls are fixedly joined.

10 Claims, 1 Drawing Sheet

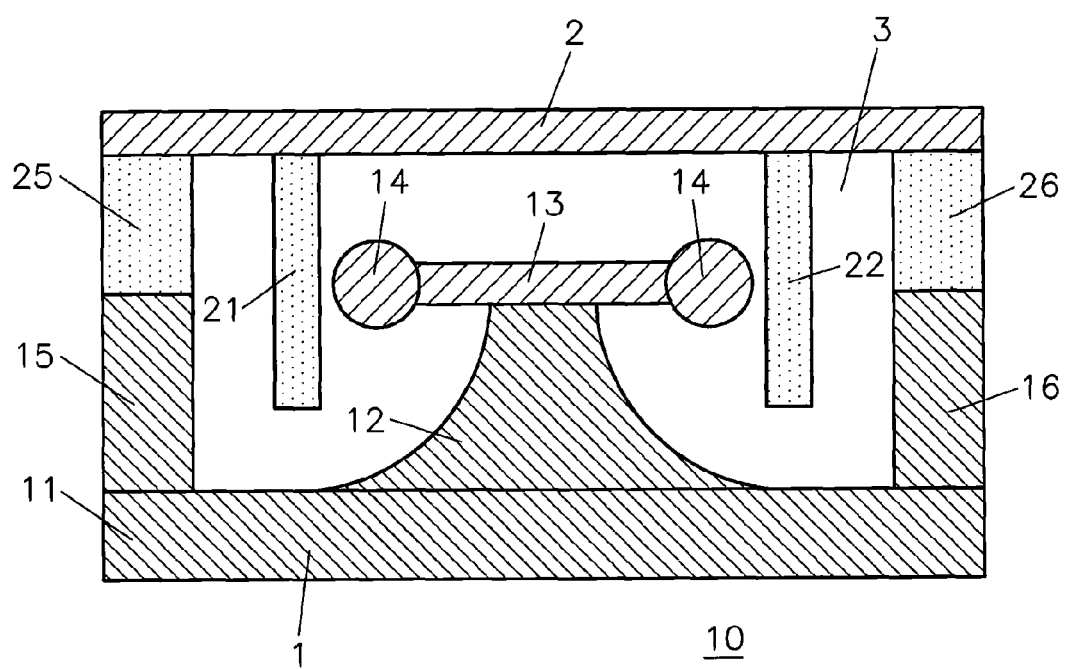

MICROOPTICAL COMPONENT AND METHOD FOR ITS MANUFACTURE

CROSS-REFERENCE TO RELATED APPLICATIONS

This application claims the benefit of priority under 35 U.S.C. 119 to European Patent Application No. 09010782.2, filed Aug. 22, 2009, which is incorporated herein by reference in its entirety.

FIELD

The present invention relates to a microoptical component for coupling laser light to microresonators, and to a method for its manufacture.

BACKGROUND

The feasibility of coupling laser light to individual microresonators is very significant with regard to using the microresonators as detectors. In *Label-Free, Single-Molecule Detection with Optical Microcavities*, Science 317, pp. 783-86, 2007, A. M. Armani, R. P. Kulkarni, S. E. Fraser, R. C. Flagan and K. J. Vahala describe the marker-free detection of single molecules that are applied to the surface of a microresonator. As a microresonator, a toroid is used which, in comparison to conventional resonator geometries, such as disks or spheres, has a quality factor (Q factor). The toroid is made of silicon dioxide ($SiO_2$) and rests on a pedestal of silicon (Si) that is disposed on a substrate that is likewise composed of Si.

In *Ultra-high-Q toroid microcavity on a chip*, Nature 421, pp. 925-28, 2003, D. K. Armani, T. J. Kippenberg, S. M. Spillane and K. J. Vahala describe the coupling of laser light to individual microresonators through thinned glass fibers. However, this entails considerable difficulty when coupling is performed to more than two microresonators. The reason for this is the thinned region of the glass fibers that is used for the coupling. The small diameter of the glass fiber (approximately 1-2 µm) makes it very sensitive to mechanical stress, and the thinned region is not completely straight due to the fabrication process. Thus, it is difficult to orient the thinned region of the glass fiber in parallel to the substrate without making contact with the substrate. Moreover, the glass fiber degrades within two to three days.

In *Silica on Si waveguides for self-aligned fibre array coupling using flip-chip Si V-groove technique*, Electronics Letters 32, pp. 1916-1917, 1996, Q. Lai, W. Hunziker and H. Melchior present what is generally referred to as the flip-chip principle for the butt-coupling of a glass fiber to waveguides.

In *Long-period gratings in polymer ridge waveguides*, Optics Express 13, pp. 1150-60, 2005, Q. Liu, K. S. Chiang and K. P. Lor describe the advantages of polymer ridge waveguides over ridge waveguides of glass or of crystals such as lithium niobate ($LiNbO_3$) or silicon.

In *Design and Applications of Optical Microsphere Resonators*, Dissertation, Helsinki University of Technology, pp. 20-21, 2003, J. Laine schematically describes bringing a first substrate, which contains a waveguide, into proximity of two microspheres that have been placed on a second substrate, based on the flip-chip principle. There is no discussion of the relative positioning of the two substrates.

SUMMARY

In an embodiment, the present invention provides a microoptical component for coupling a laser light to microresonators. The microoptical component includes at least two microresonators each having a form of an axially symmetric body disposed on a pedestal, and at least one waveguide for the laser light. The at least two microresonators are disposed on a first substrate having first side walls. The at least one waveguide is disposed on a second substrate having second side walls. The first side walls and the second side walls are fixedly joined.

BRIEF DESCRIPTION OF THE DRAWINGS

While the appended claims set forth the features of the present invention with particularity, the invention and its advantages are best understood from the following detailed description taken in conjunction with the accompanying drawings, of which:

FIG. 1 is a schematic of a microoptical component according to an embodiment the present invention.

DETAILED DESCRIPTION

Embodiments of the invention present a microoptical component for coupling laser light to microresonators, as well as a method for its manufacture, which will overcome the aforementioned disadvantages and limitations of existing approaches.

In one embodiment, a device is provided that allows laser light from at least one waveguide to be coupled to a plurality of preferably toroidal microresonators, the at least one waveguide being oriented in parallel to the substrate having the microresonators.

In addition, a device is provided that includes means for delivering a substance to be detected in a simple and defined manner into the detection zone where the microresonators are located.

An embodiment of a method is provided that enables the at least one waveguide, the plurality of microresonators, and the means for delivering the substance to be detected to be fabricated in a simplest possible manner.

In an embodiment, the invention provides a method for producing a microoptical component comprising at least two microresonators disposed on a first substrate having first side walls and at least one waveguide disposed on a second substrate having second side walls, the method comprising bringing the at least one waveguide into proximity of the at least two microresonators by turning over the second substrate so as to bring the second sidewalls into proximity of the first sidewalls so as to fixedly join the first sidewalls with the second sidewalls.

A microoptical component according to an embodiment of the present invention for coupling laser light to microresonators includes at least the following structural components:

at least one waveguide, preferably one or two waveguides for guiding laser light;

at least two microresonators, each having the form of an axially symmetric body, preferably a toroid or spheroid (ellipsoid of revolution), which may also be curved or conical in shape and be situated on a pedestal;

a first substrate on which the at least two microresonators are located and which is provided on two sides with first side walls;

a second, preferably transparent substrate on which the at least one waveguide is located and which is provided on two sides with second side walls.

In accordance with an embodiment of the present invention, the first side walls and the second side walls are permanently mechanically joined to one another.

The at least one waveguide, which is suited for guiding laser light, is preferably a ridge waveguide. In accordance with Liu et al., a polymer ridge waveguide, in particular, a ridge waveguide of polymethyl methacrylate (PMMA) is preferably suited for this purpose.

In accordance with D. K. Armani et al., the at least two microresonators each have the form of a spheroid or toroid which is situated on a pedestal.

The optical coupling of the laser light to the at least two microresonators is carried out by the at least one waveguide that is located on the second substrate. In this case, the coupling of the laser light is performed in accordance with what is generally referred to as the flip-chip principle: The substrate having the at least one waveguide is disposed in an upside-down configuration and has been brought from above into proximity of the at least two microresonators.

If the lateral distance between the at least one waveguide and the at least two microresonators assumes a value within the range of the wavelength of the light, preferably of from 400 nm to 3000 nm, the laser light is coupled through the lateral evanescent field of the at least one waveguide into the at least two microresonators. The vertical spacing between the two substrates is preferably adjusted to provide a maximum overlap of the waveguide mode and the microresonator mode, whereby the desired optical coupling of the laser light to the at least two microresonators is optimized.

Thus, in accordance with an embodiment of the present invention, the at least one waveguide is oriented in parallel to the first substrate, upon which the at least two microresonators are located, without making contact with the microresonators or the first substrate. This characteristic of an embodiment of the present invention is the prerequisite for the simultaneous optical coupling of laser light to at least two microresonators.

In one preferred embodiment, a transparent material, preferably quartz glass or PMMA, which, moreover, has a lower refractive index than the at least one waveguide, is selected for the second substrate, thereby enabling the light to be guided via total internal reflection within the at least one waveguide.

In one particular embodiment, two waveguides are provided, between which the at least two microresonators are configured. Placing a second waveguide next to the at least two microresonators makes the component suited for use as a narrow-band add-drop filter in optical telecommunications, in particular, to filter selected frequencies through the at least two microresonators and to couple the same into the second waveguide.

In accordance with an embodiment of the present invention, the first side walls and the second side walls are permanently joined to one another and, therefore, do not need to be held in place in relation to one another. This type of fastening also makes a passive adjustment possible. The two side walls are preferably made of silicon or a transparent material, preferably quartz glass or a polymer.

In one preferred embodiment, the two side walls, together with the two substrates, form a closed microfluidic channel. When the at least two microresonators are used as detectors, this configuration is preferably suited for directing a substance to be detected, from the outside, using the capillary forces occurring in the microfluidic channel, in a defined manner into a detection zone in the microfluidic channel.

A microoptical component according to an embodiment of the present invention is able to be produced, in particular, using the following method.

To produce the micro-toroids, the first substrate is first coated with a photoresist that is used as an etching mask. By irradiating and developing the resist and through subsequent melting, the substrate is patterned in such a way that at least two microresonators are formed, which each have the form of an axially symmetric body that resides on a pedestal.

To produce the at least one waveguide, a layer of a suitable material is first spin-coated onto the second substrate. Following appropriate irradiation and development, the at least one waveguide is isolated (e.g., separated to form one individual piece). A ridge waveguide is preferably produced in this manner.

An embodiment of the present invention then provides for the at least one waveguide, which is located on the second substrate, to be brought into proximity of the at least two microresonators in that the second substrate is turned over in accordance with the flip-chip principle. For the approaching process, it is advantageous that the second substrate be transparent to facilitate adjustment by a microscope.

In one preferred embodiment, the two substrates are permanently joined together in that the structuring of the two side walls is integrated in each case into the process for producing each of the two substrates. This type of embodiment provides a considerable advantage over the otherwise customary and costly bonding technique.

In one preferred embodiment, the microfluidic channel is formed by a suitable process control when both substrates are produced prior to the flip-chip approaching process. The two substrates are subsequently permanently joined together.

In one alternative embodiment, the microfluidic channel is formed using additional material, in particular adhesive agent that preferably contains epoxy resin, or adhesive film that is produced in accordance with the flip-chip process.

A fundamental advantage of a microoptical component according to an embodiment of the present invention resides in that the two substrates are permanently joined to one another and, therefore, do not need to be held in place in relation to one another. This type of fastening allows a microfluidic channel to be simply implemented and, moreover, for a passive adjustment to be performed.

In contrast to fiber optic technology, the at least one waveguide is straight and rugged and is, therefore, readily couplable to a plurality of microresonators, simultaneously and in parallel.

FIG. 1 shows schematically the design of a microoptical component 10 according to an embodiment of the present invention. A toroid 14 of $SiO_2$ is placed via a disk 13 on a pedestal 12 of silicon, pedestal 12 being permanently joined to first substrate 1 that is likewise composed of silicon. In addition, two side walls 15, 16 are affixed to first substrate 1. Two ridge waveguides 21, 22 of PMMA are located on second substrate 2 of quartz glass. Moreover, second substrate 2 is provided with two side walls 25, 26.

To fabricate the microresonators that are shaped as microtoroids, an oxidized silicon wafer is first coated with a photoresist. The resist is subsequently irradiated and developed using electron beam lithography. In the next step, the structured photoresist is used as an etching mask, the glass having been patterned using buffered hydrofluoric acid. In the following step, the photoresist is removed using acetone. Subsequently thereto, the disks obtained are undercut-etched using xenon difluoride in order to be melted in the last step with the aid of a $CO_2$ laser.

Alternatively, an oxidized silicon wafer is first coated with a photoresist that is subsequently irradiated and developed using electron beam lithography. The disks obtained are then undercut-etched using xenon difluoride, to finally be melted using a micro-hotplate.

At the same time that the micro-toroids are fabricated, first substrate 1 is provided with two side walls 15, 16.

The ridge waveguide of PMMA is produced on a quartz glass substrate upon which a layer of PMMA is spin-coated, and the solvent is expelled in a subsequent back step. The two waveguides are subsequently irradiated using UV lithography with the aid of a chromium/quartz mask. The lithographic edges of the two waveguides are defined in a second irradiation step.

Subsequently thereto, the waveguides are developed using a developer solution composed of methyl isobutyl ketone (MIBK) and isopropanol (IPA) in the mixing ratio of 1:1. Alternatively, what is generally referred to as a GG developer, composed of 20% deionized water, 60% 2-(2-butoxy-ethoxy) ethanol, 15% tetrahydro-1-4-oxazine and 5% 2-aminoethanol, and a BDG stopper, composed of 20% deionized water, 80% 2-(2-butoxyethoxy) ethanol are used.

In the last step, the waveguides are sliced into individual pieces using a wafer saw, the saw cut being made at a distance of approximately 20 μm from the waveguide edge. Here as well, second substrate 2 is provided with two side walls 25, 26 at the same time that ridge waveguides 21, 22 are produced.

In accordance with an embodiment of the present invention, ridge waveguides 21, 22, which are located on second substrate 2, are then brought into proximity of the plurality of microresonators situated on first substrate 1, in that second substrate 2 is turned over in accordance with the flip chip principle. In this context, the vertical distance between the two substrates is adjusted to provide a maximum overlap of the waveguide mode and the microresonator mode. In this manner, the optical coupling of the laser light to the at least two microresonators is adjusted as optimally as possible.

During this approaching process, the two side walls 25, 26 of second substrate 2 are brought in a concurrent operation into such proximity of the two sides walls 15, 16 of first substrate 1 that they are permanently joined together, as shown in FIG. 1. Thus, microfluidic channel 3 is formed together with first substrate 1 and second substrate 2.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A microoptical component for coupling a laser light to microresonators, comprising:
   at least two microresonators each having a form of an axially symmetric body disposed on a pedestal, the at least two microresonators being disposed on a first substrate having first side walls; and
   at least one waveguide for the laser light, the at least one waveguide being disposed on a second substrate having second side walls, wherein the first side walls and the second side walls are fixedly joined.

2. The microoptical component as recited in claim 1, wherein the first side walls and the second side walls are joined to one another so as to form a microfluidic channel in which the at least one waveguide and the at least two microresonators are disposed.

3. The microoptical component as recited in claim 1, wherein the first and second side walls include at least one of silicon, quartz glass, and a transparent polymer.

4. The microoptical component as recited in claim 1, wherein the second substrate is transparent and has a lower refractive index than the at least one waveguide.

5. The microoptical component as recited in claim 1, wherein the at least one waveguide is a polymer ridge waveguide.

6. The microoptical component as recited in claim 1, wherein the at least one waveguide comprises two waveguides suited for incoupling the laser light, wherein the at least two microresonators are disposed between the two waveguides.

7. The microoptical component as recited in claim 1, wherein a lateral distance between the at least one waveguide and the at least two microresonators is 400 nm to 3000 nm.

8. The microoptical component as recited in claim 1, wherein the at least two microresonators each include a form of at least one of a toroid and a spheroid.

9. A method for producing a microoptical component comprising at least two microresonators disposed on a first substrate having first side walls and at least one waveguide disposed on a second substrate having second side walls, the method comprising bringing the at least one waveguide into proximity of the at least two microresonators by turning over the second substrate so as to bring the second sidewalls into proximity of the first sidewalls so as to fixedly join the first sidewalls with the second sidewalls.

10. The method for producing a microoptical component as recited in claim 9, wherein the second sidewalls are brought into proximity of the first sidewalls so that, together with first substrate and the second substrate, the first and second sidewalls form a microfluidic channel.

* * * * *